United States Patent [19]

Filomeno

[11] Patent Number: 4,692,261

[45] Date of Patent: Sep. 8, 1987

[54] SKIN BLEACHING DETERGENT BAR

[75] Inventor: Vito G. Filomeno, Mount Arlington, N.J.

[73] Assignee: Warner-Lambert Company, Morris Plains, N.J.

[21] Appl. No.: 811,602

[22] Filed: Dec. 20, 1985

[51] Int. Cl.$^4$ .......................... C11D 1/12; C11D 3/20; A61K 7/135
[52] U.S. Cl. .................................. 252/105; 252/94; 252/545; 252/550; 252/551; 252/404; 252/557; 252/DIG. 16; 424/62; 514/728
[58] Field of Search ............... 252/550, 551, 557, 545, 252/105, 94, DIG. 16, 404; 424/62

[56] References Cited

U.S. PATENT DOCUMENTS

| | | | |
|---|---|---|---|
| 3,060,097 | 10/1962 | Fellows | 424/62 |
| 3,855,150 | 12/1974 | Weris | 252/404 |
| 4,044,160 | 8/1977 | Erickson et al. | 426/330 |
| 4,100,097 | 7/1978 | O'Roark | 252/145 |
| 4,136,166 | 1/1979 | Barnett et al. | 424/62 |
| 4,295,985 | 10/1981 | Petrow et al. | 252/105 |
| 4,466,955 | 8/1984 | Calvo et al. | 424/62 |

FOREIGN PATENT DOCUMENTS 89398  7/1980  Japan.

OTHER PUBLICATIONS

McCutcheon's, "Functional Materials", The Manufacturing Confectioner Publishing Co., 1983, p. 24.

Primary Examiner—Prince E. Willis
Attorney, Agent, or Firm—Daniel A. Scola, Jr.; Henry C. Jeanette; Gary M. Nath

[57] ABSTRACT

A synthetic detergent bar is provided containing hydroquinone as a skin bleaching agent. The bar is maintained at a pH of between about 4 and 7 and includes a compressed mixture of a synthetic anionic detergent such as sodium cocoyl isethionate, sodium lauryl sulfoacetate and sodium methyl cocoyl tourate; hydroquinone, a stabilizer for said hydroquinone such as tertiary butyl hydroquinone, water, a buffer which maintains the pH of the bar at about 4 to about 7 and excipients such as waxes, paraffin, dextrin and starches. Because of the maintenance of low pH and the presence of a stabilizer, hydroquinone is not oxidized and thus the bar is characterized by an extended shelf life.

14 Claims, No Drawings

SKIN BLEACHING DETERGENT BAR

BACKGROUND OF THE INVENTION

This invention is concerned with a detergent bar containing hydroquinone as a skin bleaching ingredient.

Melanin is a dark, sulfur-containing pigment normally found in the skin, hair, eyes and certain nerve cells which is produced in cells called melanocytes. Melanin is produced in the melanocytes by the conversion of the amino acid tyrosine in the presence of the enzyme tyrosinase. It is generally believed that the number of melanocytes varies widely among individuals.

There frequently occurs in a given individual a localized area of the skin wherein the malanin density within the melanocytes is markedly increased resulting in a skin color in the area affected far darker than normal background skin color. These localized areas of hyperpigmentation are commonly referred to as Brown Spots, Age Spots or Liver Spots. Women are also subject to these melanin-dense spots as a result of child bearing and taking birth control pills. The skin disfigurement which results from these areas of hyperpigmentation, which may be more or less permanent in character, is often a source of great distress to the individual.

In the past there have been described a number of topical skin compositions containing one or more ingredients capable of reducing the melanin density in the melanocytes of the skin. Such ingredients are termed depigmentation agents or bleaching agents and are absorbed into the lower layers of the skin in order to inhibit the formation of melanin in the melanocytes.

The most frequently described bleaching agents are based on hydroquinone or derivatives of hydroquinone, Benzyloxyphenol, the monobenzylether of hydroquinone, is one such hydroquinone derivative which has found wide application as a bleaching agent. In U.S. Pat. No. 3,060,097 for example, a skin bleaching composition is described comprising benzyloxyphenol, sodium hypochlorite, a penetrant and a soothing agent such as a lanolin compound and a solvent acting also as a penetrant. Unfortunately benzyloxyphenol is not metabolized to any great degree when absorbed into the skin and is associated with incidents of irreversible depigmentation simulating vitiligo (patches of depigmentation often having a hyperpigmented border and enlarging slowly). In addition benzyloxyphenol is transported by the lymph system and may cause irreversible depigmentation in areas of the body far removed from the site of application. Methoxyphenol, another ether of hydroquinone, has also been used in cosmetic compositions for depigmentation but is relatively insoluble in the aqueous media which is a constituent of many cosmetic formulations.

A substituted isomer of hydroquinone, 4-isopropyl catechol has also been employed as the active ingredient in cosmetic formulations to effect skin depigmentation (see South African Pat. Appl. 716,890). Mono and difatty acid esters of hydroquinone have also been employed in topical skin depigmentation compositions and are described in European patent Application No. 82301102.8.

Hydroquinone itself is conveniently used in cosmetics for the treatment of hyperpigmentation since it is effective, soluble in water and readily metabolized and excreted from the body. Hydroquinone, however, when present in an alkaline environment is unstable and is oxidized to the quinone form imparting an accompanying browning effect to any composition in which it is incorporated. To prevent such oxidation it is necessary to incorporate an antioxidant into the hydroquinone-containing composition such as ascorbic acid or butylated hydroxy anisole to modify the hydroquinone itself. Hydroquinone is also a skin irritant.

Alcoholic-gel cosmetic sticks such as stick deodorants offer a medium for cosmetic bleaching using hydroquinone since it is soluble in alcohol. However, the gelling agents used in such sticks are soaps such as sodium stearate and their alkalinity readily and rapidly decomposes hydroquinone.

Hydroquinone has also been stabilized by incorporating it into an anhydrous medium. In U.S. Pat. No. 4,466,955, a non-aqueous cosmetic skin preparation is described in which hydroquinone is dissolved in polypropoxylated or polyethoxylated fatty ethers and this anhydrous solution is incorporated into an extended oil and wax non-aqueous cosmetic base. In such an anhydrous oil-wax base the hydroquinone is more stable and less prone to oxidation since oxygen is less soluble in waxes than in water and oxygen from the air does not reach the wax-dissolved hydroquinone as readily as if it were solubilized in water. The polyalkoxylated agents act as solubilizing agents in the hydroquinone and are themselves cosmetic skin penetration agents which allow controlled release of hydroquinone.

The present invention, on the other hand, provides a non-cosmetic synthetic detergent bar for use on the skin containing hydroquinone as a depigmentation agent and water which is maintained at acid to neutral pH to prevent oxidation of the hydroquinone. The bar is characterized by having a long shelf life.

SUMMARY OF THE INVENTION

The synthetic detergent bar of the invention comprises a compressed mixture of synthetic detergents, hydroquinone as the depigmentation agent, a stabilizer for the hydroquinone, water, and a buffer to maintain the pH of the bar from about 4 to about 7. The bar also contains excipients such as paraffin, waxes, dextrin, starches and other ingredients.

The synthetic detergents employed in the bar of the invention are anionic detergents which are active and stable at low pH's and non-irritating to the skin. The preferred detergents are coconut-oil fatty acid esters of sodium isethionate and sodium methyl taurate such as sodium cocoyl isethionate and sodium methyl cocoyl taurate; acyl N-methyltaurides; fatty alcohol sulfates; monoalkyl sulfosuccinates; alkyl sulfoacetates such as sodium lauryl sulfoacetate; glyceryl ester sulfates; and acylglutamates, among others. A mixture or blend of these compounds is also suitable. Generally the amount of detergent should comprise from 20 to 45% by weight of the total bar and preferably from 25% to 30% by weight. By avoiding conventional soap formulations which are blends of fatty acids and alkali high pH's are avoided which contribute to hydroquinone oxidation. The use of these synthetic detergents makes it feasible to formulate the bar at a lower pH, thus maintaining the chemical stability of hydroquinone.

The hydroquinone is incorporated into the bar in amounts to effect depigmentation. Generally amounts of between 1% and 5% by weight of the total bar and preferably about 1.5 to about 3.0% and most preferably 2% by weight are suitable.

Water is employed in the bar formulation at levels of from 15% to 20% by weight of the total bar and preferably between about 10% and 15% by weight. The water serves to dissolve the hydroquinone and acts as a binder and plasticizer.

In order to maintain the pH of the bar at about 4 to about 7 and thus to enhance hydroquinone stability a buffer is dissolved in the water. Such buffers include citric acid, lactic acid or other similar organic acid.

Generally the buffer should comprise from about 1% to 5% by weight of the total bar and preferably about 2% by weight.

To further maintain the stability of the hydroquinone against oxidation a stabilizer is added to the bar composition. Of particular effectiveness as a stabilizer is tertiary butyl hydroquinone (TBHQ). The tertiary butyl hydroquinone may be used alone or in combination with other stabilizers such as sodium sulfite, sodium bisulfite and alpha tocopherol. The sulfite, bisulfite and tocopherol stabilizers are effective but not to the degree of TBHQ. Generally the total amount of stabilizer or combinations thereof should not exceed about 0.6% by weight of the total bar. When TBHQ is used in combination with other stabilizers each component stabilizer should be present in amounts between 0.1% and 0.3% by weight of total bar.

Other ingredients such as paraffin, waxes, starches and dextrin are added to the bar to provide desirable physical and aesthetic qualities. These ingredients should constitute between 50% and 60% by weight of the total weight of the bar.

The paraffin ingredient is preferably a fully refined petroleum wax having a melting point ranging from about 130° F. to about 140° F. This wax is odorless and tasteless and meets FDA requirements for use as coatings for food and food packages. Such paraffins are readily available commercially. A very suitable paraffin can be obtained, for example, from the Standard Oil Company of Ohio under the tradename Factowax R-133.

The paraffin ingredient is used in the product to impart plasticity, firmness, and processability in soap equipment. It also provides a glossy look and smooth feel to the bar.

The paraffin ingredient is optionally supplemented by a microcrystalline wax. A suitable microcrystalline wax has a melting point ranging, for example, from about 140° F. to about 160° F., preferably from about 145° F. to about 155° F. The wax preferably should meet the FDA requirements or food grade microcrystalline waxes. A very suitable microcrystalline wax was obtained from Witco Chemical Company under the tradename Multiwax X-145A. The microcrystalline wax preferably is present in the bar in an amount ranging from about 0.5% to about 5% by weight. The microcrystalline wax ingredient imparts pliability to the bar at room temperatures.

The combination of powdered starch and dextrin ingredients provide a unique filler system to help provide, with the waxes, a base to carry the detergent.

The powdered starch ingredient is preferably selected from the group consisting of pregelatinized starch and non-gelling starch, and very preferably the total starch ingredient used is present in the bar in an amount ranging from about 7.5% to about 13.5% by weight. The pregelatinized starch is preferably a gelling pregelatinized starch as precooked corn starch which has been dried and powdered. A very suitable gelling pregelatinized starch is obtained from CPC International under the tradename Amidex (B-511). The gelling pregelatized starch is very tacky, providing binding and imparting slip feel to the bar. This starch works particularly well when coconut-oil fatty acid ester of sodium isethionate is used as a detergent ingredient. The non-gelling starch is preferably a 100% amylopectin starch. A very suitable 100% amylopectin starch is obtained from National Starch under the tradename Amioca. The 100% amylopectin starch imparts very desirable processing chractertistics to the formula. This starch works particularly well when sodium lauryl sulfoacetate is used as a detergent ingredient. The two types of starches can be used in conjunction with other in a total amount within the aforedescribed broad range to help provide optimum slip-feel and processability. A bar including both types of starches can include, for example, from about 5% to about 10% by weight gelling pregelatinized starch and from about 2% to about 4% by weight non-gelling 100% amylopectin starch.

The dextrin ingredient is dextrin having a water solubility ranging from about 25% to about 85% (about 25% to about 85% by weight of the dextrin dissolves in water, and the rest is insoluble). Very preferably, the total amount of dextrin used is present in the bar in an amount ranging from about 12.5% to about 25% by weight. Very preferably, the dextrin ingredient is selected from the group consisting of dextrin having a water solubility ranging from about 25% to about 55%, and dextrin having a water solubility ranging from about 60% to about 85%. Dextrin having a water solubility ranging from about 25% to about 55%, with its higher insoluble content, can be used to control washing wear rate and to improve processability. A dextrin of this type is obtained from National Starch and Chemical Corporation under the tradename Nadex 341 (it is a white powdered corn dextrin and has an average water solubility of about 40%). Dextrin having a water solubility ranging from about 60% to about 85% imparts a smooth slip-feel to the bar but introduces higher washing wear rate and tends to lower processability. A dextrin of this type is obtained from National Starch and Chemical Corporation under the tradename Nadex 419 (it is a white powdered corn dextrin and has an average water solubility of about 70%). By using these two types of dextrins in conjunction (both types together being used in a total amount within the aforedescribed broad range), optimum conditions can be achieved for bar feel, washing wear rate and processability. Very preferably, the two types of dextrins are used in conjunction with each other in the same bar, and dextrin having a water solubility ranging from about 25% to about 55% is present in the bar in an amount ranging from about 2% to about 20% by weight and dextrin having a water solubility ranging from about 60% to about 85% is present in the bar in an amount ranging from about 5% to about 20% by weight with the total of the two types of dextrin being present in the bar in an amount ranging from about 12.5% to about 25% by weight. The dextrin water solubilities herein are in 72° F. water.

Sodium chloride is optionally included. It is used for example, at a level ranging from about 0.5% to about 4% by weight, for processing purposes. It is, for example, of positive assistance in making a premix of water and powdered starch(es) before crutcher mixing (see processing described below).

The pH of the bar preferably falls in range of about 4.5 to about 6.5.

While bars produced according to this invention have demonstrated no deterioration due to bacterial activity, it is recognized that dextrin content particularly can support bacterial growth. To obviate this possibility, antimicrobials, e.g. methyl and propyl parabens can optionally be included, for example, at a level ranging from about 0.25% to about 1% by weight.

Added bar slip-feel is readily obtained by incorporating such agents as high molecular weight polymers of ethylene oxide (e.g. a polymer acid under the tradename Polyox WSR 205 by Union Carbide) and high molecular weight polymers of acrylamide (e.g. a polymer sold under the tradename Gelamide F by American Cyanamid).

The ingredients can be processed to form bars using conventional soap line equipment. For example, processing can be carried out as follows. First, premelted waxes (microcrystalline wax, if any is used, and paraffin) are added to the crutcher. Lauric diethanolamide may be also added into the crutcher in premelted form. The temperature in the mix is then adjusted to be in the 190° F.–200° F. range. Next, the powdered detergent is added and this lowers the temperature of the mix. Then crutcher agitation is started and heat is supplied. This is continued until a smooth slurry is obtained at 160° F.–180° F. Next, the dextrins are introduced. Then crutcher agitation is started again, and heating is supplied; this is continued until a uniform slurry is obtained at 160° F.–180° F. Then, a pre-mixed powdered starch water slurry is added, and again crutcher agitation is continued and heat is supplied until the total contents are uniform at 160° F.–180° F. Lactic or other acid (to modify bar pH) is readily added with the starch water slurry. Following this the temperature is lowered and the hydroquinone stabilizers are added and mixed. The resulting mix is dropped on a cold roll and taken off in the form of a chip or flake. These (chips or flakes) are passed through a plodder. The effluent from the plodder is collected in soap buggies. The buggies feed the conventional soap equipment line consisting of an amalgamotor, mills, vacuum plodder and soap press.

Bars formulated in accordance with the present invention show minimal discoloration after storage for 3 months or more. Assays of hydroquinone in these bars indicated minimal oxidation.

In order to more completely describe the present invention the following Examples are provided. Such Examples are given to demonstrate specific embodiments of the invention and do not limit the scope of the invention.

EXAMPLES 1–3

These Examples demonstrate the preparation of a synthetic detergent bar containing hydroquinone as the depigmentation agent and also demonstrates the efficacy of tertiary butyl hydroquinone as the preferred stabilizer.

In all Examples a detergent bar was prepared by the procedure described above. In Example 1 a mixture of tertiary butyl hydroquinone, sodium sulfite and sodium bisulfite was employed as the stabilizer; in Example 2 only sodium sulfite and sodium bisulfite was employed and in Example 3 alpha tocopherol was employed as the sole stabilizer. The active synthetic detergents were sodium cocoyl isethionate and sodium lauryl sulfoacetate in all Examples. Paraffin, waxes, dextrin and starches were also added. Table 1 below lists the ingredients and, corresponding amounts in weight percent of the bar.

TABLE 1

| Ingredient | 1 | 2 | 3 |
| --- | --- | --- | --- |
| Cocyl Isethionate | 28.00 | — | — |
| Sodium Lauryl Sulfoacetate | — | 28.00 | — |
| Combination * of detergents | — | — | 28.00 |
| Water | 15.00 | 15.00 | 15.00 |
| Hydroquinone | 2.00 | 2.00 | 2.00 |
| Buffer | 2.00 | 2.00 | 2.00 |
| Sodium Sulfite | 0.30 | 0.30 | — |
| Sodium Bisulfite | 0.20 | 0.20 | — |
| Tertiarybutyl Hydroquinone (TBHQ) | 0.10 | — | — |
| Alpha Tocopherol | — | — | 0.20 |
| Waxes, Starches, Dextrin | 52.4 | 52.5 | 52.8 |

* Cocyl isethionate and sodium lauryl sulfoacetate in equal amounts.

After storage for three months at 37° C. and 45° C. and one year of storage at room temperature it was found that the bar of Example 1 showed minimal discoloration. Assays for hydroquinone indicated little or no oxidation as indicated below, thereby confirming stability. The bars of Examples 2 and 3 were rated satisfactory in terms of organoleptic properties but showed greater discoloration. The bar in Example 1 was used on the skin intermittently over a period of about three (3) weeks and was shown to have skin bleaching properties.

| | Hydroquinone Assay | | |
| --- | --- | --- | --- |
| | Initial | 1 Mo./45° C. | 6 Mos./ Room Temp. |
| Hydroquinone U.S.P. | 2.2% | 2.2% | 2.2% |

I claim:

1. A detergent bar composition having a pH of about 4 to about 7 comprising a compressed mixture of:
   (a) an anionic detergent selected from the group consisting of sodium cocoyl isethionate, sodium methyl cocyl taurate and mixtures thereof;
   (b) hydroquinone in amounts to effect depigmentation;
   (c) tertiary butyl hydroquinone in amounts to maintain the stability of said hydroquinone against oxidation;
   (d) a buffer which maintains the pH of said composition at about 4 to about 7;
   (e) a paraffin, wax, starch, or dextrin constituent, or mixtures thereof; and
   (f) water.

2. The composition of claim 1 which further comprises an additional stabilizer, in amounts to maintain the stability of said hydroquinone against oxidation, selected from the group consisting of sodium sulfite, sodium bisulfite, alpha tocopherol and mixtures thereof.

3. The composition of claim 1 wherein the amount of detergent comprises from 20% to 45% by weight of said total composition.

4. The composition of claim 1 wherein the amount of hydroquinone comprises from about 1% to 5% by weight of said total composition.

5. The composition of claim 1 wherein the amount of tertiary butyl hydroquinone does not exceed about 0.6% by weight of said total composition.

6. The composition of claim 1 wherein the amount of water is from about 15% to 20% by weight of said total composition.

7. The composition of claim 2 wherein the tertiary butyl hydroquinone and said stabilizer are each present in amounts of 0.1% to 0.3% by weight of the total bar such that the total amount of tertiary butyl hydroquinone and stabilizer does not exceed about 0.6% by weight of the total bar.

8. The composition of claim 1 wherein the amount of said detergent comprises from 20% to 45% by weight of said total composition, the amount of hydroquinone comprises from about 1% to 5% by weight of said total composition, the amount of tertiary butyl hydroquinone does not exceed about 0.6% by weight of said total composition, the amount of said constituent is 50% to 60% by weight of said total composition, and the amount of said water is from about 15% to 20% by weight of said total composition.

9. The composition of claim 8 further comprising an additional stabilizer selected from the group consisting of sodium sulfite, sodium bisulfite, alpha tocopherol, and mixtures thereof, wherein said tertiary butyl hydroquinone and said stabilizer are each present in amounts of 0.1% to 0.3% by weight of the total bar such that the total amount of tertiary butyl hydroquinone and stabilizer does not exceed about 0.6% by weight of said total composition.

10. The composition of claim 9 wherein said stabilizer is a mixture of sodium sulfite and sodium bisulfite.

11. A detergent bar composition having a pH of about 4 to about 7 for use as a skin bleaching agent comprising a mixture of:
    (a) an anionic detergent which is active at a pH of about 4 to about 7;
    (b) hydroquinone in amounts to effect depigmentation;
    (c) tertiary butyl hydroquinone in amounts to maintain the stability of said hydroquinone; and
    (d) an additional stabilizer in amounts to maintain the stability of said hydroquinone against oxidation.

12. The composition of claim 11 wherein said stabilizer of (d) is selected from the group consisting of sodium sulfite, sodium bisulfite, alpha tocopherol and mixtures thereof.

13. The composition of claim 11 wherein said stabilizer of (d) is a mixture of sodium sulfite and sodium bisulfite.

14. The composition of claim 11 wherein the amount of said detergent comprises from 20% to 45% by weight of the total bar, the amount of said hydroquinone comprises from about 1% to 5% by weight of the total bar, and said tertiary butyl hydroquinone and said stabilizer of (d) are each present in amounts of 0.1% to 0.3% by weight of the total bar such that the total amount of tertiary butyl hydroquinone and stabilizer does not exceed about 0.6% by weight of the total bar.

* * * * *

UNITED STATES PATENT AND TRADEMARK OFFICE
CERTIFICATE OF CORRECTION

PATENT NO.  : 4,692,261

DATED       : September 8, 1987

INVENTOR(S) : Vito G. Filomeno

It is certified that error appears in the above-identified patent and that said Letters Patent is hereby corrected as shown below:

In the Specification:

Column 1, line 16, "malanin" should read --melanin--.

Column 3, line 52, "or" should read --for--.

Column 4, line 13, "chractertistics" should read --characteristics--.

Signed and Sealed this

Twenty-sixth Day of April, 1988

Attest:

DONALD J. QUIGG

*Attesting Officer*   *Commissioner of Patents and Trademarks*